United States Patent [19]

Quash

[11] 4,355,102

[45] Oct. 19, 1982

[54] AGGLUTINATION TESTS FOR DETECTING INFLUENZA VIRUSES, AND REAGENTS FOR CARRYING OUT THESE TESTS

[75] Inventor: Gérard Quash, Sainte Foy-Les Lyon, France

[73] Assignee: Institut National de la Sante et de la Recherche Medicale, INSERM, Paris, France

[21] Appl. No.: 128,232

[22] Filed: Mar. 5, 1980

[30] Foreign Application Priority Data

Mar. 6, 1979 [FR] France .................................. 79 05703

[51] Int. Cl.$^3$ .......................... C12Q 1/70; C12Q 1/34; G01N 33/00
[52] U.S. Cl. ........................................... 435/5; 435/7; 435/18; 435/174; 435/810; 23/230 B; 424/12
[58] Field of Search ...................... 435/5, 6, 7, 18, 174, 435/188, 200, 206; 424/12; 23/230 B

[56] References Cited

U.S. PATENT DOCUMENTS

| | | | |
|---|---|---|---|
| 3,826,613 | 7/1974 | Parikh et al. ...................... | 23/230 B |
| 3,963,441 | 6/1976 | Dietrich ................................ | 435/5 |
| 4,080,264 | 3/1978 | Cohen et al. ........................ | 435/5 |
| 4,116,777 | 9/1978 | Takatsy et al. ..................... | 435/5 |
| 4,140,662 | 2/1979 | Reckel et al. ...................... | 435/181 |
| 4,217,338 | 8/1980 | Quash ................................... | 424/1 |
| 4,282,315 | 8/1981 | Luderer et al. ..................... | 435/5 |

FOREIGN PATENT DOCUMENTS

| | | |
|---|---|---|
| 2653267 | 7/1977 | Fed. Rep. of Germany . |
| 2378094 | 8/1978 | France . |

OTHER PUBLICATIONS

Quash, "Biological Reactants Consisting of Solid Supports to which are Coupled Organic Compounds Containing Carbohydrate Residues", Chem. Absts., vol. 90 (1979), Absts. No. 148119z.

Holmquist, "Preparation of Sepharose-Bound α-Ketosides of N-Acetylneuraminic Acid and their Interaction with *Vibrio cholerae* Neuraminidase, Chem. Absts., vol. 82, No. 11, (1975), p. 158, Abs. No. 69667h.

Thraenhart, et al., "Standardization of a Rapid Modified Micro-Neuraminidase-Inhibition Test (Essen—NIT) for Influenza Virus-Neuraminidase Antibody Assay and Comparison with W.H.O. Method", J. Biol. Stand., vol. 4 (1976). pp. 225-241.

Santer, et al., "A Rapid Assay for Neuraminidase", Brochim. Biophys. Acta., vol. 523, (1978), pp. 435-442.

Cuatrecasas et al., "Purification of Neuraminidases from *Vibrio Cholerae, Clostridium Perfringens* and Influenzia Virus by Affinity Chromatography", Biochem. Biophys. Res. Comm., vol. 44, (1971), No. 1, pp. 178-184.

Warren, "The Thiobarbituric Acid Assay of Sialic Acids", J. Biol. Chem., vol. 234, No. 8, (1959), pp. 1971-1975.

*Primary Examiner*—Thomas G. Wiseman
*Attorney, Agent, or Firm*—Browdy and Neimark

[57] ABSTRACT

The present invention relates to a new test for detecting influenza viruses. This test comprises: 1- the addition of influenzia virus or of allantoic liquid containing said virus to neuraminidase substrate containing at least one sialic acid group. The substrate is fixed by covalent coupling to an appropriate insoluble solid support, it being understood that said substrate may be formed by all types of mucoproteins, oligosaccharides, mucopolysaccharides or mucolipids comprising at least one sialic acid group capable of being used as a neuraminidase substrate; 2- incubation of the influenza virus with its substrate for an appropriate length of time; 3- then reading the reaction.

16 Claims, No Drawings

AGGLUTINATION TESTS FOR DETECTING INFLUENZA VIRUSES, AND REAGENTS FOR CARRYING OUT THESE TESTS

BACKGROUND OF THE INVENTION

The present invention relates to new agglutination tests for detecting influenza viruses and to reagents for carrying out these tests.

Influenza, a contagious, endemic and epidemic illness, practically the only treatment for which is vaccination, poses serious prophylactic problems because of the antigenic variability of the influenza viruses. Generally, the detection of influenza viruses and the resulting diagnosis of influenza are important for three essential reasons:

in the epidemiologic sphere in keeping a check on the degree of immunity of populations during an influenza epidemic;

in the preventative field, for identifying strains to be introduced into the vaccines;

in the clinical field, finally, for the accurate diagnosis of the influenza infection, in particular for the abnormal and rare clinical forms.

This is why techniques have been proposed for some years for detecting the influenza virus. These techniques may be classed into two main categories, biological techniques and immunological techniques, these latter comprising the conventional hemagglutination techniques and techniques for measuring the titre of antibodies capable of inhibiting the activity of the neuraminidase. The biological technique which consists in isolating and identifying the virus itself after culture in embryonated eggs or on monkey kidney cells is long and requires a highly-qualified staff. On the other hand, the immunological techniques are easy to implement and so are more widely used than the biological technique, in particular the hemagglutination inhibition method. Hemagglutination is visible only in the case where the serum analyzed does not contain non specific antibodies which mask the hemagglutinating sites. However, these immunological techniques may present difficulties which are sometimes difficult to overcome, namely:

the presence of non-specific inhibitors, variations in the biological and antigenic characteristics of the viruses, variations in the quality of the erythrocytes.

On the other hand, the inhibition of the enzymatic activity of the neuraminidase (Mucopolysaccharide N-acetylneuraminylhydrolase of the influenza viruses; international classification 3.2.1.18) is a very good method for detecting the specific anti-neuraminidase antibodies of a strain of the influenza virus. The neuraminidase is identified by inhibition of the activity of the enzyme by means of an anti-serum prepared against the reference virus antigens. The amount of influenza virus is measured by determining the amount of neuraminidase (compare in particular the work of P. CUATRECASAS and G. ILLIANO in Biochem. and Biophys. Res. Communications (1971), 44, 1, 178-184). The determination of the neuraminidase comprises two principal steps:

(a) the step of incubating the virus alone or the virus pretreated by means of the anti-serum, with fetuin—the substrate of the neuraminidase—for 18 hours at 37° C.;

(b) the step of determination of the sialic acid released by the action of the neuraminidase, by means of the technique of WARREN (L. WARREN, J. Biol. Chem. 234 (1959) 1971). This latter determination is very long and complicated and comprises several steps which require numerous reagents, accurate heating times and finally colorimetric measurements after extraction of the thiobarbituric derivative of the oxidized sialic acid in ButOH/HCl. The routine determination of several samples is then particularly laborious for determination of sialic acid with a view to detecting the neuraminidase, all the following Articles: Journal of Biological Standardization 1976 4, 225–241 O. THAENHART and E. K. KUWERT and Biochimica et Biophysica Acta, 523 (1978) 435–442 U. V. SANTER, J. YEE-FOON and M. C. GLICK).

The aim of the present invention is accordingly to provide a new test for detecting influenza viruses which combines the specificity of the enzymatic reaction with agglutination techniques. It is easy to carry out and gets over the disadvantages of these two methods taken separately.

SUMMARY OF THE INVENTION

The present invention provides a process for detecting influenza viruses, characterized in that an agglutination test is carried out by:

adding influenza virus or allantoic liquid containing said virus, to a substrate of the neuraminidase comprising at least one sialic acid group, which substrate is fixed by covalent coupling on an appropriate insoluble solid support, it being understood that said substrate may be formed by all types of mucoproteins, mucopolysaccharides, oligosaccharides or mucolipids comprising at least one sialic acid group able to act as a substrate for the neuraminidase;

incubation of the influenza virus with its substrate for an appropriate length of time;

then reading the reaction.

According to an advantageous embodiment of the test for detecting flu viruses in accordance with the invention, the desired dilutions of the influenza virus or of the allantoic liquid and the neuraminidase substrate coupled by covalency to said solid support are put into suspension in an appropriate buffer then, before reading the reaction, incubation is carried out for the desired length of time.

According to another advantageous embodiment of the test for detecting influenza viruses in accordance with the invention, the reaction medium comprising the desired influenza virus or allantoic liquid dilutions, the neuraminidase substrate coupled by covalency to a solid support and the buffer, are introduced into the wells of an agglutination microplate. After incubation, the reading of the reaction is effected directly in the agglutination plate, by observation with the naked eye by means of a diffuse light source.

According to one particularly advantageous embodiment of the invention, the neuraminidase substrate fixed on the support is fetuin.

In accordance with the invention, the insoluble solid support is taken particularly from the group comprising latex spheres, agarose or dextran gel beads activated glass marbles, or similar.

According to an advantageous embodiment of said solid support, this latter carries lateral chains comprising a terminal group —$NH_2$.

According to an advantageous embodiment of the invention, the solid support comprises carboxyl groups on which said lateral chains carrying a terminal —NH₂ group are fixed by covalency.

According to another advantageous embodiment of the invention, the solid support is formed by latex acid-hydrazide spheres of formula I below:

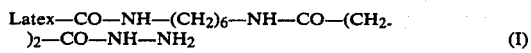

According to another advantageous embodiment of the invention, the solid support is formed by latex spheres terminating in p-aminobenzoate side chains the diazotization of which produces links with tyrosine residues of glycoproteins containing sialic acid residues in the sugar moieties.

The preparation of these different supports has been described in the French Patents and Certificates of Addition No. 75 34627; 76 08966; 76 25898 (all of which correspond to U.S. Pat. No. 4,217,338); and 77 01889.

In accordance with the invention, these supports may also be prepared by a process comprising the following steps:

(a) treatment of the latex-carboxyl spheres with hexamethylenediamine (HMD) dissolved extemporaneously, in the presence of -ethyl-3-3-dimethylaminopropyl-carbodiimide (EDC) added as a solid in three separate additions within 24 hours;

(b) succinylation of the NH₂ groups by addition of succinic anhydride at a pH greater than 8;

(c) treatment with hydrazine hydrochloride in the presence of EDC.

Thus, the process for detecting influenza viruses in accordance with the invention does not detect the neuraminidase by determination of the sialic acid produced during the enzymatic reaction, but consists in measuring the complex formed between the enzyme and its substrate, i.e. fetuin, immobilized on latex spheres, which gives rise to agglutination of the spheres.

Schematically the reaction is the following:

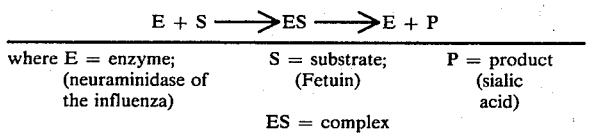

| where E = enzyme; (neuraminidase of the influenza) | S = substrate; (Fetuin) ES = complex | P = product (sialic acid) |
|---|---|---|

Thus the same specificity is obtained as with the enzymatic reaction, but with the important advantage of eliminating the subsequent steps which are required, in accordance with the prior art, for showing up the released sialic acid.

The present invention also provides a reagent for implementing the agglutination test in accordance with the invention, formed by a neuraminidase substrate comprising at least one sialic acid group, fixed by covalent coupling to an appropriate insoluble solid support.

In accordance with the invention, said substrate is chosen from the group which comprises the mucoproteins, the mucopolysaccharides, the oligosaccharides and the mucolipids comprising at least one sialic acid group.

Also in accordance with the invention, said substrate is coupled by covalency to an insoluble solid support of the above-mentioned type, previously activated by diazotation by means of NaNO₂ in an acid solution.

For preparing the reagent in accordance with the invention, the substrate of the neuraminidase is coupled to the insoluble solid support, in an appropriate buffer, after having possibly fixed on said support lateral chains comprising a terminal —NH₂ group and after having possibly activated said support by diazotation with NaNO₂ in an acid solution.

Besides the above arrangements, the invention comprises other arrangements which will become clear from the following description.

The invention aims more particularly at detecting influenza viruses by means of a simple, rapid, reproducible very sensitive and relatively inexpensive process, the means for implementing this process and the general processes in which are included the process and the reagents in accordance with the present invention.

The invention will be better understood from the complement of description which follows and which refers to one example for implementing the test in accordance with the invention.

It will however be understood that this example is given solely by way of illustration of the invention but forms in no way a limitation thereof.

DESCRIPTION OF THE PREFERRED EMBODIMENTS OF THE INVENTION

EXAMPLE

1-Preparation of the solid support: latex-acid-hydrazide

Hydrazide chains are coupled to the surface of carboxylated latex spheres.

The synthesis takes place according to the following diagram:

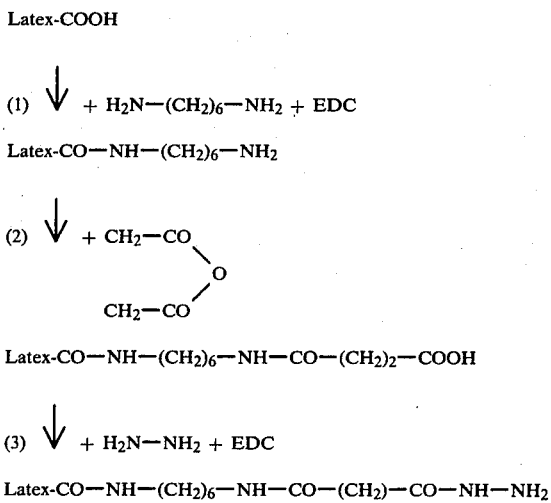

1 g of latex spheres K318C (manufactured by RHONE-POULENC, Aubervilliers-France) having a diameter of 0.85 μm and containing 5.5×10¹⁵ COOH/mg, washed by filtration on a Millipore filter (diameter 450 mm, porosity 0.6 micrometers) is taken up by 2 ml of 0.1 M borate-HCl pH 8.1 buffer in a 30 ml centrifuge tube.

To that is added 230 micromoles of hexamethylenediamine (HMD) dissolved extemporaneously in 25 ml of BBS buffer (0.01 M borate-HCl pH 8.1 0.15 M NaCl).

The tube is placed on an oscillating agitator at 4° C. and receives in three additions spaced over 24 hours, 1-ethyl-3-3-dimethylaminopropylcarbodiimide (EDC) in the solid state, the final concentration being 0.05 M EDC.

The washings are carried out with BBS buffer by three cycles of centrifugation of 15 minutes each at 12,000 g.

The pellet is taken up in a 0.1 M borate-HCl pH 8.1 buffer and the $NH_2$ groups are succinylated by the addition of 1 mmole of solid succinic anhydride. After a night in contact, the tube is centrifuged, the pellet taken up again with the Borate buffer and the treatment is renewed.

After three treatments, the latex are washed by three cycles of centrifugation. The succinylation must take place at a pH greater than 8, which is adjusted if necessary with 1 N NaOH. This is why in this step, the Borate buffer replaces the BBS.

The latex pellet obtained is taken up in 2 ml of 0.1 M Borate pH 8,1; 2 ml of a 0.2 M hydrazine-HCl pH 7.5 solution are then added. The suspension is carefully homogenized and the volume is brought to 25 ml with BBS pH 8.1 and then the EDC is added to a final concentration of 0.05 M. The preparation is incubated overnight at +4° C. on an oscillating agitator. The hydrazine and EDC treatment is renewed.

The cycle of three washings is followed by a prolonged dialysis. Thus $3.6 \times 10^{15}$ hydrazide groups (titrated by diazotation) were found per mg of latex, i.e. a yield of 66%.

2-Coupling of the Latex-Acid-Hydrazide with the Feutin (a) Activation of the latex-acid-hydrazide To 200 mg of hydrazide latex in suspension in water, 4 ml of 4% $NaNO_2$ and 10 ml of 2 N HCl are added. The mixture is maintained under agitation in an ice bath for 15 minutes. At the end of this period, the mixture is rapidly filtered on a Millipore 0.65 micron filter and washed with an ice-cold buffer containing a 0.1 M borate-HCl pH 8.1 to eliminate the excess $HNO_2$, $NaNO_2$ and HCl.

The diazotized latex is loosened from the Millipore by vortex agitation and ultrasonic treatment.

(b) Coupling properly speaking

To 200 mg of activated latex, there are added 100 mg of fetuin dissolved in the 0.1 M borate-HCl, pH 8.1 buffer in a total volume of 20 ml. The mixture is left in contact with gentle agitation for 48 hours at 4° C. At the end of this period, the latex-fetuin is recovered by centrifugation at 10,000 g for 20 minutes, and washed in two successive cycles of centrifugation in a buffer containing 0.14 M NaCl, 0.1 M glycine-NaOH pH 8.1. At the end of the washings, the latex is taken up in this latter buffer and resuspended by an ultrasonic treatment.

From the determination of the protein remaining in the supernatant and its comparison to the quantity introduced, the quantity of fetuin in fixed/mg of latex for four different preparations of latex-fetuin, at was found to be $162 \pm 35$ micrograms, 3-Agglutination test of latex-fetuin on microplate Buffer: 0.14 M NaCl, 0.2% BSA (bovine albumin serum), 0.05% Triton X 100 0.1 M glycine-NaOH pH 8.1.

Microplates having 96 holes with V-shaped wells are coated with silicone before use to reduce the phenomena due to surface tension.

Into each well are put in the following order:
(a) 50 microliters of the above buffer,
(b) 50 microliters of the different dilutions of the influenza virus or of allantoic liquid diluted in 0.14 M NaCl,
(c) 50 microliters of latex-fetuin diluted to 350 micrograms of latex/ml in 0.14 M NaCl, 0.1 M glycine pH 8.1.

A first control of latex alone is made with 50 microliters of 0,14 M NaCl; a second control contains the same quantity of latex, out in the presence of different dilutions of allantoic liquid containing no influenza virus.

The plate is closed with a cover, surrounded with adhesive tape and placed on a plate agitator in the incubator at 37° C. for 1 hour, followed by an incubation time of one night at rest at the temperature of the laboratory.

Reading of the Plate

The plates are placed on a negative slide viewer and are read against a black background.
It may be carried out in two ways:

First Method negative reaction (symbolized by - in Table I below), there is no agglutination: presence of a pellet of latex spheres forming a distinct well-defined point.
positive reaction (symbolized by +), there is agglutination, i.e. a deposit of latex spheres in the form of a diffuse poorly-defined layer.

Second Method

It is carried out after including the plate for 15 to 20 minutes.
negative reaction: the non-agglutinated spheres flow and form a whitish trail
positive reaction: the agglutinated spheres do not flow.

For successful interpretation of the test, it is necessary that all the controls, i.e. the latex control in the presence of the buffer and the latex control in the presence of allantoic liquid alone, are negative, i.e. that they will have to form a pellet of spheres which, after being inclined, will flow.

TABLE I

|  | Dilutions | | | | | | | | |
| --- | --- | --- | --- | --- | --- | --- | --- | --- | --- |
|  | 1/10 | 1/20 | 1/40 | 1/80 | 1/160 | 1/320 | 1/640 | T | T |
| Allantoic liquid containing the influenza A virus | + | + | + | + | + | + | − | − | − |
| control allantoic liquid | − | − | − | − | − | − | − | − | − |

The reaction between the influenza A and the latex-fetuin is then specific.

To show the sensitivity of the test for detecting influenza viruses in accordance with the invention, it has been compared with tests at present used. The results of the comparative tests carried out are shown in Table II below.

TABLE II

COMPARATIVE TESTS FOR DIFFERENT STRAINS OF INFLUENZA BETWEEN THE TITERS OBTAINED BY ENZYMATIC QUANTITY DETERMINATION AND BY AGGLUTINATION

| | TITERS | | |
|---|---|---|---|
| | Conventional HEMAGGLUTININ | NEURAMINIDASE by enzymatic determination | by latex agglutination |
| EGG CULTURES | | | |
| Vict. 3/75 (9.9.77) 79 all | 5120 | 10 | 320 |
| Texas 1/77 (6.3.78) 35 all | 5120 | 15 | 160 |
| USSR 90/77 (6.3.78) 30 + 31 all | 40 | 20 | 80 |
| MRC 2 (14.4.78) mell all | >10240 | 20 | 320 |
| England 42/72 (29.3.78) mell all | 1280 | 10 | 160 |
| England HOO 658 (17.3.78) 2 all | >10240 | 20 | 320 |
| England HOO 743 (3.4.78) 5 all | >10240 | 15 | 160 |
| England HOO 746 (14.4.78) 12 all | 320 | 60 | 160 |
| CULTURES ON CELLS | | | |
| England p2 RSV 658 (27.2.78) | 5 | 0 | 80 |
| England p4 RSV 743 (13.3.78) | 5 | 0 | 40 |
| England p4 RSV 746 (23.3.78) | 10 | 0 | 10 |

It is clear from this comparative table that the process of the invention is very sensitive in comparison with the conventional neuraminidase determination process by the WARREN method.

In fact, whereas it is practically impossible to detect the neuraminidasic activity of in the culture medium of cells by the enzymatic method, the latex-fetuin method reveals the neuraminidase.

Table III below reproduces the results of a series of tests carried out for quantifying anti-neuraminidase antibodies and for showing the specificity of these antibodies on the agglutination of the latex-fetuin reagents by the influenza viruses.

These tests were carried out on a microplate, the influenza virus tested being a SINGAPORE 57 influenza virus diluted to 1/50 in 0.14 M NaCl.

The antiserums tested were diluted in 0.14 M NaCl.

The tests were carried out as follows:
there is placed in each well:
25 microliters of the antiserum dilution to be tested
+25 microliters of Singapore 1/50 it is incubated at 22° C. under rotary agitation for 1 hour.

Into each well is then added:
50 microliters of a buffer having the following composition:

| | | |
|---|---|---|
| NaCl | 0.14M | |
| Gly—NaOH | 0.10M | pH 8.1 |
| BSA | 0.20% | |
| Triton X 100 | 0.05% | |

+50 microliters of latex-fetuin spheres diluted to 350 micrograms latex/ml stirring is carried out for 1 hour at 37° C. then the mixture is left for a night at 22° C.

Then the plate is read as described in the above example.

TABLE III

Specificity tests of the anti-neuraminidase antibodies by agglutination inhibition

| Antiserums anti | Origin | DILUTIONS | | | | | | | | CONTROLS | |
|---|---|---|---|---|---|---|---|---|---|---|---|
| | | 1/160 | 1/320 | 1/640 | 1/1280 | 1/2560 | 1/5120 | 1/10240 | 1/20480 | 1/50 allantoic liquid alone | 1/50 allantoic liquid + Singapore 57 |
| Texas influenza 77 | Ferret | + | + | + | + | + | + | + | + | − | − | + | + |
| Texas 77 neuraminidase | Rabbit | − | + | + | + | + | + | + | + | − | − | + | + |
| Singapore 57 influenza | Ferret | − | − | − | − | + | + | + | + | | | | |
| Singapore 57 neuraminidase | Rabbit | − | − | − | − | − | − | + | + | | | | |
| USSR 77 influenza | Rabbit | − | + | + | + | + | + | + | + | | | | |
| SM 1 influenza | Ferret | + | + | + | + | + | + | + | + | | | | |
| SM 1 influenza | Rabbit | − | + | + | + | + | + | + | + | | | | |

This table clearly shows that the inhibition of the agglutination only takes place with the anti-Singapore 57 homologous serums.

It follows from the preceding description that whatever the modes of use, implementation and application adopted, a process for detecting influenza viruses is obtained and consequently a diagnosis test for influenza, which present as compared to the previously-known processes having the same aim (biological, immunological or enzymatic) very important advantages, apart from those which have already been mentioned and particularly:

A-Rapidity

This method is very easy to carry out.

It is rapid, is easily carried out in half a day; the following day, the reading requires no handling unlike enzymatic titration of the neuraminidase, which is long.

The reagents, i.e. the solution of latex spheres and the buffer, keep very well at +4° C. It is then not necessary to prepare them again for each assay contrary to the enzymatic determination of the neuraminidase which requires an extemporaneous preparation of the reagents.

It requires less constant supervision, once the dilutions have been effected and, with the plate filled, the handling is practically finished.

B-Reproducibility

Three viral strains tested simultaneously were taken again twice in succession, these three strains being:
Vict Influenza A 3/75 (9.9.77) 79 all
USSR Influenza A 90/77 (6.3.78) 30+31 all
Texas Influenza A 1/77 (6.3.78) 35 all
The tests gave the following results:

| Test 1: | Vict | 320 | Test 2: | Vict | 320 |
|---|---|---|---|---|---|
| | USSR | 80 | | USSR | 80 |
| | Texas | 160 | | Texas | 160 |

There is then reproducibility of the results. (The strains were frozen, at −20° C. inbetween the two determinations).

C-Sensitivity

The sensitivity of the method was tested by determining the maximum dilution to which the virus can be subjected for reaction with fetuin bound to latex spheres, and by comparing this dilution with the neuraminidase titer obtained by enzymatic determination according to the WARREN method.

Therefore the agglutination titrations on latex-fetuin, the neruaminidase titrations by the WARREN method, as well as the hemagglutinin titration by the current method with fowl erythrocytes were carried out concurrently for different strains, these strains coming from egg cultures or monkey kidney cell cultures. The results obtained, shown in Table II above, clearly bring out the sensitivity of the test in accordance with the invention.

D-Economy (1) Reading system:

The reading requires no sophisticated apparatus; it is done directly on the agglutination plates, with the naked eye, by means of an oblique light, on a black background, supplied by a negative slide viewer for example.

(2) Stability of the preparation:

The latex-fetuin preparations may be kept in a glycine NaCl buffer, +0.01% of Na azide at +4° C. for more than 6 months.

E-Other Applications

The latex-fetuin reagent may also be used for the determination of the anti-neuraminidase antibodies in human serum.

It is apparent that within the scope of the invention, modifications and different arrangements can be made other than are here disclosed. The present disclosure is merely illustrative with the invention comprehending all variations thereof.

What is claimed is:

1. A process for detecting influenza viruses by means of an agglutination test, comprising:
   adding influenza virus or allantoic liquid containing said virus, to a reagent comprising a neuraminidase substrate capable of being hydrolyzed by neuraminidase and having at least one sialic acid group and being a mucoprotein, mucopolysaccharide, oligosaccharide or mucolipid, said substrate being fixed by covalent coupling to an insoluble solid support selected from the group consisting of latex spheres, agarose or dextran gel beads, and activated glass marbles;
   incubating the influenza virus with the substrate for a time sufficient to permit an agglutination reaction to take place between the neuraminidase and the solid support-coupled substrate; and
   then measuring the degree of agglutination.

2. The process as claimed in claim 1, wherein the desired dilutions of influenza virus or of allantoic liquid and the neuraminidase substrate covalently coupled to said solid support, are put into suspension in an appropriate buffer at pH 8.1, then, before measuring the degree of agglutination, incubation is carried out for said sufficient length of time.

3. The process as claimed in claim 2, wherein the reaction medium, comprising the desired dilutions of the influenza virus or of the allantoic liquid, the neuraminidase substrate covalently coupled to a solid support and the buffer, is introduced into the wells of an agglutination microplate, then incubated, after which the measurement of the degree of agglutination is carried out directly in the agglutination plate, with the naked eye, by means of a diffuse light source.

4. The process as claimed in claim 1, wherein the neuraminidase substrate fixed on the support is fetuin.

5. The process as claimed in claim 1, wherein the solid support of said reagent carries lateral chains having a terminal NH$_2$ group.

6. The process as claimed in claim 1, wherein the solid support of said reagent includes carboxyl groups on which are fixed by covalency lateral chains carrying a terminal NH$_2$ group.

7. The process as claimed in claim 6, wherein the solid support of said reagent is formed by latex acid-hydrazide spheres of the formula I below:

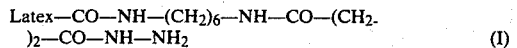

Latex—CO—NH—(CH$_2$)$_6$—NH—CO—(CH$_2$)$_2$—CO—NH—NH$_2$     (I)

8. The process as claimed in claim 6, wherein the solid support of said reagent is formed by latex spheres terminating in p-aminobenzoate side chains the diazotization of which produces links with tyrosine residues of glycoproteins containing sialic acid residues in the sugar moieties.

9. The process as claimed in claim 1, wherein the support of said reagent is one which has previously been activated by diazotization by means of NaNO$_2$ in an acid solution.

10. A process for preparing a reagent for use in an agglutination test for detecting influenza viruses, comprising the following steps:
   (a) treatment of latex-acid spheres with hexamethylenediamine (HMD) in the presence of ethyl-3,3-dimethylaminopropylcarbodiimide (EDC) added in the solid state in three additions within 24 hours,
   (b) succinylation of the NH$_2$ groups by addition of succinic anhydride at a pH greater than 7,
   (c) treatment with hydrazine hydrochloride in the presence of EDC, and
   (d) covalent coupling of an amino acid residue of a neuraminidase substrate capable of being hydrolyzed by neuraminidase and having at least one sialic acid group, at the end of the chain, on the spheres of latex acid-hydrazide obtained in the preceding step, by contacting said spheres with said substrate dissolved in a buffer at pH 8.1.

11. The process as claimed in claim 10, wherein the covalent coupling of said substrate on the spheres of latex acid-hydrazide is preceded by activation of said spheres by diazotization by means of NaNO$_2$ in an acid solution.

12. A process for determining anti-neuraminidase antibodies in a serum, comprising:
   adding serial dilutions of the serum to a known type and amount of influenza virus or allantoin fluid containing said virus and a reagent comprising a neuraminidase substrate capable of being hydrolyzed by neuraminidase and having at least one sialic acid group and being a mucoprotein, mucopolysaccharide, oligosaccharide or mucolipid, said substrate being fixed by covalent coupling to an insoluble solid support selected from the group consisting of latex spheres, agarose or dextran gel beads, and activated marbles;
   incubating for a time sufficient to permit an agglutination reaction to take place between the virus and the substrate; and
   measuring the degree of agglutination to determine the degree, if any, to which said agglutination is inhibited by anti-neuraminidase antibodies.

13. A reagent for use in an agglutination test for detecting influenza viruses, comprising fetuin fixed by covalent coupling, via an amino acid residue thereof, to an insoluble solid support selected from the group consisting of latex spheres, agarose or dextran gel beads, and activated glass marbles.

14. The reagent in accordance with claim 13 wherein said solid support carries lateral chains having a terminal NH$_2$ group.

15. A reagent for use in an agglutination test for detecting influenza viruses, comprising a neuraminidase substrate capable of being hydrolized by neuraminidase and having at least one sialic acid group and being a mucoprotein, mucopolysaccharide, oligosaccharide or mucolipid, said substrate being fixed by covalent coupling, via an amino acid residue thereof, to an insoluble solid support comprising latex acid-hydrazide spheres of the formula:

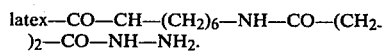

latex—CO—CH—(CH$_2$)$_6$—NH—CO—(CH$_2$)$_2$—CO—NH—NH$_2$.

16. A reagent for use in an agglutination test for detecting influenza viruses, comprising a neuraminidase substrate capable of being hydrolyzed by neuraminidase and having at least one sialic acid group and being a mucoprotein, mucopolysaccharide, oligosaccharide or mucolipid, said substrate being fixed by covalent coupling, via an amino acid residue thereof, to an insoluble solid support comprising latex spheres terminating in p-aminobenzoate side chains, the diazotization of which produces links with tyrosine residues of glycoproteins containing sialic acid residues in the sugar moieties.

* * * * *